United States Patent
Park et al.

(10) Patent No.: US 11,998,316 B2
(45) Date of Patent: Jun. 4, 2024

(54) SYSTEM AND METHOD FOR MEASURING BODY INFORMATION, POSTURE INFORMATION, AND RANGE OF MOTION

(71) Applicant: Ha Yeon Park, Seoul (KR)

(72) Inventors: Ha Yeon Park, Seoul (KR); Jae Hoon Jeong, Seoul (KR)

( * ) Notice: Subject to any disclaimer, the term of this patent is extended or adjusted under 35 U.S.C. 154(b) by 339 days.

(21) Appl. No.: 16/999,091

(22) Filed: Aug. 21, 2020

(65) Prior Publication Data

US 2021/0052199 A1 Feb. 25, 2021

(30) Foreign Application Priority Data

Aug. 23, 2019 (KR) .......................... 10-2019-0103915

(51) Int. Cl.
*A61B 5/11* (2006.01)
*A61B 5/00* (2006.01)
*H04N 13/239* (2018.01)

(52) U.S. Cl.
CPC .......... *A61B 5/1121* (2013.01); *A61B 5/0077* (2013.01); *A61B 5/1128* (2013.01);
(Continued)

(58) Field of Classification Search
None
See application file for complete search history.

(56) References Cited

U.S. PATENT DOCUMENTS

| 2012/0000300 A1* | 1/2012 | Sunagawa | A61B 5/4023 73/865.4 |
| 2012/0183939 A1* | 7/2012 | Aragones | A63B 24/0062 434/247 |

(Continued)

FOREIGN PATENT DOCUMENTS

| JP | 2014-068714 | 4/2014 |
| JP | 2015-109937 | 6/2015 |

(Continued)

OTHER PUBLICATIONS

English Specification of 10-2017-0315003.
(Continued)

*Primary Examiner* — Benjamin S Melhus
(74) *Attorney, Agent, or Firm* — ANTONIO HA & U.S. PATENT, LLC

(57) ABSTRACT

According to an embodiment, a system comprises a target image display forming a skeleton image of a subject on a grid pattern with a predetermined unit length and coordinates via image processing by a three-dimensional (3D) depth camera, specifying, on the skeleton image, feature points corresponding to the subject's joints, a reference point corresponding to a measurement target among the feature points, and a motion point corresponding to a joint moving with respect to the reference point, and generating a connection line connecting the feature points and an information processor obtaining the body information from the skeleton image using the feature points, the connection line, the grid pattern, and a gravity line and median line of the subject, evaluating the posture information according to a preset posture classification criterion, and measuring the joint motion range by tracking motion of the motion point with respect to the reference point.

2 Claims, 10 Drawing Sheets

(52) U.S. Cl.
CPC ............ *A61B 5/4561* (2013.01); *A61B 5/486* (2013.01); *A61B 5/743* (2013.01); *H04N 13/239* (2018.05)

(56) References Cited

U.S. PATENT DOCUMENTS

| | | | | | |
|---|---|---|---|---|---|
| 2012/0183940 | A1* | 7/2012 | Aragones | ............... | A61B 5/744 434/247 |
| 2012/0190505 | A1* | 7/2012 | Shavit | ............... | A63B 24/0062 482/8 |
| 2012/0268592 | A1* | 10/2012 | Aragones | ............. | A61B 5/1118 702/19 |
| 2012/0271143 | A1* | 10/2012 | Aragones | ................ | G09B 5/02 600/595 |
| 2012/0277891 | A1* | 11/2012 | Aragones | ............ | G09B 19/003 700/91 |
| 2013/0115583 | A1* | 5/2013 | Gordon | ................. | G16H 20/60 434/247 |
| 2013/0115584 | A1* | 5/2013 | Gordon | ................. | A63B 69/00 434/247 |
| 2013/0251192 | A1* | 9/2013 | Tu | ......................... | G06V 10/85 382/103 |
| 2013/0268205 | A1* | 10/2013 | Aragones | ........... | A63B 24/0062 702/19 |
| 2013/0324368 | A1* | 12/2013 | Aragones | ............. | A61B 5/6807 482/8 |
| 2013/0338802 | A1* | 12/2013 | Winsper | ............. | A63B 24/0075 700/92 |
| 2014/0228985 | A1* | 8/2014 | Elliott | ..................... | A61B 5/11 700/91 |
| 2015/0025419 | A1* | 1/2015 | Aaberg | ................. | A61B 5/743 600/595 |
| 2015/0320343 | A1* | 11/2015 | Utsunomiya | ........ | A61B 5/4824 600/595 |
| 2015/0324637 | A1* | 11/2015 | Utsunomiya | .......... | G16H 20/70 382/107 |
| 2018/0020954 | A1* | 1/2018 | Lillie | .................. | A61B 5/4585 600/476 |
| 2018/0153445 | A1* | 6/2018 | Noda | .................. | A61B 5/4884 |
| 2020/0051682 | A1* | 2/2020 | Flaherty | ................ | G16H 20/30 |
| 2022/0262487 | A1* | 8/2022 | Aragones | ............. | A61B 5/6807 |

FOREIGN PATENT DOCUMENTS

| | | |
|---|---|---|
| JP | 2016-513983 | 5/2016 |
| KR | 10-2017-0099715 | 9/2017 |
| KR | 10-2017-0135003 | 12/2017 |
| KR | 10-2019-0023628 | 3/2019 |
| KR | 10-2019-0044952 | 5/2019 |

OTHER PUBLICATIONS

English Specification of 10-2019-0044952.
English Specification of 2014-068714.
English Specification of 2015-109937.
English Specification of 2016-513983.
English Specification of 10-2017-0099715.
English Specification of 10-2019-0023628.

* cited by examiner

<Stereo Camera>

<Structured pattern method>

<Sagittal plane>

<Frontal plane>

<Horizontal plane>

(a)          (b)

123

(a)            (b)

SYSTEM AND METHOD FOR MEASURING BODY INFORMATION, POSTURE INFORMATION, AND RANGE OF MOTION

CROSS-REFERENCE TO RELATED APPLICATION(S)

This application claims priority to Korean Patent Application No. 10-2019-0103915 filed in the Korean Intellectual Property Office on Aug. 23, 2019, the disclosure of which is incorporated by reference herein in its entirety.

TECHNICAL FIELD

Embodiments of the disclosure relate to systems and methods for measuring body information, posture information, and joint motion range.

DISCUSSION OF RELATED ART

Currently, 350 million people around the world are suffering from scoliosis, which is a structural change in the spinal joint, and resultant muscle pain and postural misalignment, limitations on the joint motion range and body asymmetry-related disease. The population suffering from the disease is increasing by 3% every year.

A common method for examining and evaluating people with musculoskeletal-related pain is to check the joint motion range and muscular strength.

A restriction on the range of motion of a specific joint prevents functional movement from occurring and causes compensatory movement (compensation action), resulting in structural damage to the joint area and hence pain.

Even though the human body differs from person to person, everyone is exercising in the same way.

This way does not take into account the characteristics of each person, giving the body both advantages and disadvantages.

Therefore, a need exists for providing a more correct and optimal exercise method through accurate measurement of an individual's joint motion range.

SUMMARY

According to embodiments of the disclosure, there is provided a system and method for measuring body information, posture information, and joint motion range, which may more accurately measure the length, posture, and joint motion range of a body and, based thereupon, propose the optimal exercise method to each individual.

According to an embodiment, a system for measuring body information, posture information, and a joint motion range comprises a target image display forming a skeleton image of a subject on a grid pattern with a predetermined unit length and coordinates via image processing by a three-dimensional (3D) depth camera, specifying, on the skeleton image, feature points corresponding to the subject's joints, a reference point corresponding to a measurement target among the feature points, and a motion point corresponding to a joint moving with respect to the reference point, and generating a connection line connecting the feature points and an information processor obtaining the body information from the skeleton image using the feature points, the connection line, the grid pattern, and a gravity line and median line of the subject, evaluating the posture information according to a preset posture classification criterion, and measuring the joint motion range by tracking motion of the motion point with respect to the reference point.

The information processor may include a body information obtaining unit obtaining the body information including left-right symmetry information and physical numerical information about the subject's body length, angle, or ratio from the skeleton image using the feature points, the connection line, the grid pattern, the gravity line, and the median line, a posture information evaluating unit obtaining and evaluating the posture information from the skeleton image according to the preset posture classification criterion, using the gravity line and the median line, and a joint motion range measuring unit measuring the joint motion range by tracking the motion of the motion point with respect to the reference point.

The joint motion range measuring unit may remeasure a joint motion range by sensing motion of the feature points except for the reference point and the motion point of the feature points or excludes an angle for the motion from the measured joint motion range.

The joint motion range measuring unit may remeasure the joint motion range upon sensing at least one of a movement of the gravity line or the median line and a movement of a first connection point, except for the motion point, extended and connected via the connection line from the reference point among the feature points.

Upon sensing a movement of a second connection line adjacent to the reference point and connected via the connection line from the reference point among the feature points, the joint motion range measuring unit may measure the joint motion range by calculating a first angle formed by the movement of the motion point and a second angle formed by the movement of the second connection point and subtracting the second angle from the first angle.

The joint motion range measuring unit may remeasure the joint motion range upon sensing a movement of a third connection point corresponding to a limb end joint adjacent to the motion point and connected via the connection line from the reference point among the feature points.

The system may further comprise an exercise feedback provider providing exercise recommendation information based on the body information, the posture information, and the joint motion range.

According to an embodiment, a method for measuring body information, posture information, and a joint motion range comprises a target image displaying step for forming a skeleton image of a subject on a grid pattern with a predetermined unit length and coordinates via image processing by a 3D depth camera, a target joint specifying step for specifying, on the skeleton image, feature points corresponding to the subject's joints, a reference point corresponding to a measurement target among the feature points, and a motion point corresponding to a joint moving with respect to the reference point, and generating a connection line connecting the feature points, and a body information obtaining step for obtaining the body information from the skeleton image using the feature points, the connection line, the grid pattern, and a gravity line and median line of the subject, a posture information evaluating step for evaluating the posture information according to a preset posture classification criterion preset using the feature points, the connection line, the grid pattern, the gravity line, and the median line, and a joint motion range measuring step for measuring the joint motion range by tracking motion of the motion point with respect to the reference point.

The body information obtaining step may include obtaining the body information including left-right symmetry information and physical numerical information about the subject's body length, angle, or ratio from the skeleton image using the feature points, the connection line, the grid pattern, the gravity line, and the median line. The posture information evaluating step may include obtaining and evaluating the posture information from the skeleton image according to the preset posture classification criterion, using the gravity line and the median line. The joint motion range measuring step may include measuring the joint motion range by tracking the motion of the motion point with respect to the reference point.

The joint motion range measuring step may include remeasuring a joint motion range by sensing motion of the feature points except for the reference point and the motion point of the feature points or excludes an angle for the motion from the measured joint motion range.

The joint motion range measuring step may include remeasuring the joint motion range upon sensing at least one of a movement of the gravity line or the median line and a movement of a first connection point, except for the motion point, extended and connected via the connection line from the reference point among the feature points.

The joint motion range measuring step may include, upon sensing a movement of a second connection line adjacent to the reference point and connected via the connection line from the reference point among the feature points, measuring the joint motion range by calculating a first angle formed by the movement of the motion point and a second angle formed by the movement of the second connection point and subtracting the second angle from the first angle.

The joint motion range measuring step may include remeasuring the joint motion range upon sensing a movement of a third connection point corresponding to a limb end joint adjacent to the motion point and connected via the connection line from the reference point among the feature points.

The method may further comprise an exercise feedback providing step for providing exercise recommendation information based on the body information, the posture information, and the joint motion range.

According to embodiments of the disclosure, it is possible to provide an exercise feedback system via measurement of body information, posture information, and joint motion range, which may more accurately measure the length, posture, and joint motion range of a body and, based thereupon, propose the optimal exercise method to each individual.

DETAILED DESCRIPTION

The terms used herein are briefly described, and the present disclosure is then described in detail.

For use in embodiments of the present disclosure, common terms widely used as possible have been chosen considering functions in the disclosure, but the terms may be varied depending on the intent of one of ordinary skill in the art or case laws or the advent of new technologies. In certain cases, some terms may be arbitrarily selected by the applicant, and in such case, their detailed definitions may be given in the relevant parts thereof. Accordingly, the terms used herein should be determined based on their meanings and the overall disclosure, rather than by the terms themselves.

When an element "includes" another element, the element may further include the other element, rather excluding the other element, unless particularly stated otherwise. Further, the terms "unit," "module," or "part" as used herein denote a unit or a circuit or circuitry processing at least one function or operation, and a unit, module, or part may be implemented in hardware (e.g., as a circuit or as circuitry), software, or a combination thereof.

Embodiments of the present disclosure are now described with reference to the accompanying drawings in such a detailed manner as to be easily practiced by one of ordinary skill in the art. However, the present disclosure may be implemented in other various forms and is not limited to the embodiments set forth herein. For clarity of the disclosure, irrelevant parts are removed from the drawings, and similar reference denotations are used to refer to similar elements throughout the specification.

As used herein, the term "joint motion range" or "motion range" may refer to a range of motion of a joint or a range in which a joint can be moved.

Figure 1:
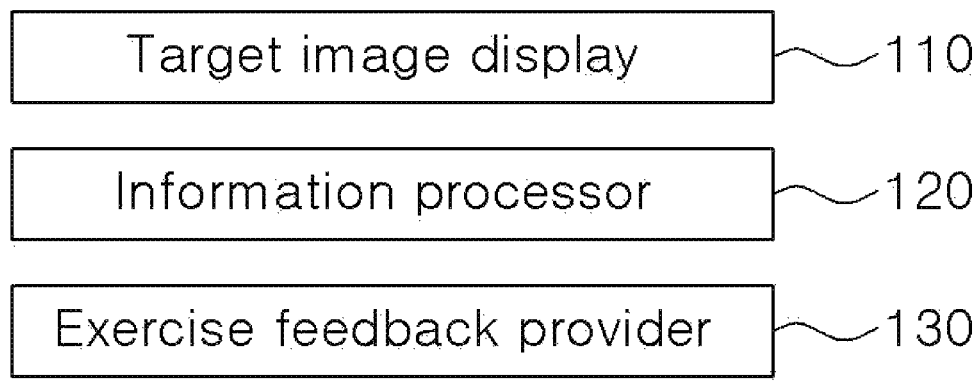
FIG. 1 is a block diagram illustrating an overall configuration of an exercise feedback system via measurement of body information, posture information, and joint motion range according to an embodiment of the disclosure.
Figure 2:
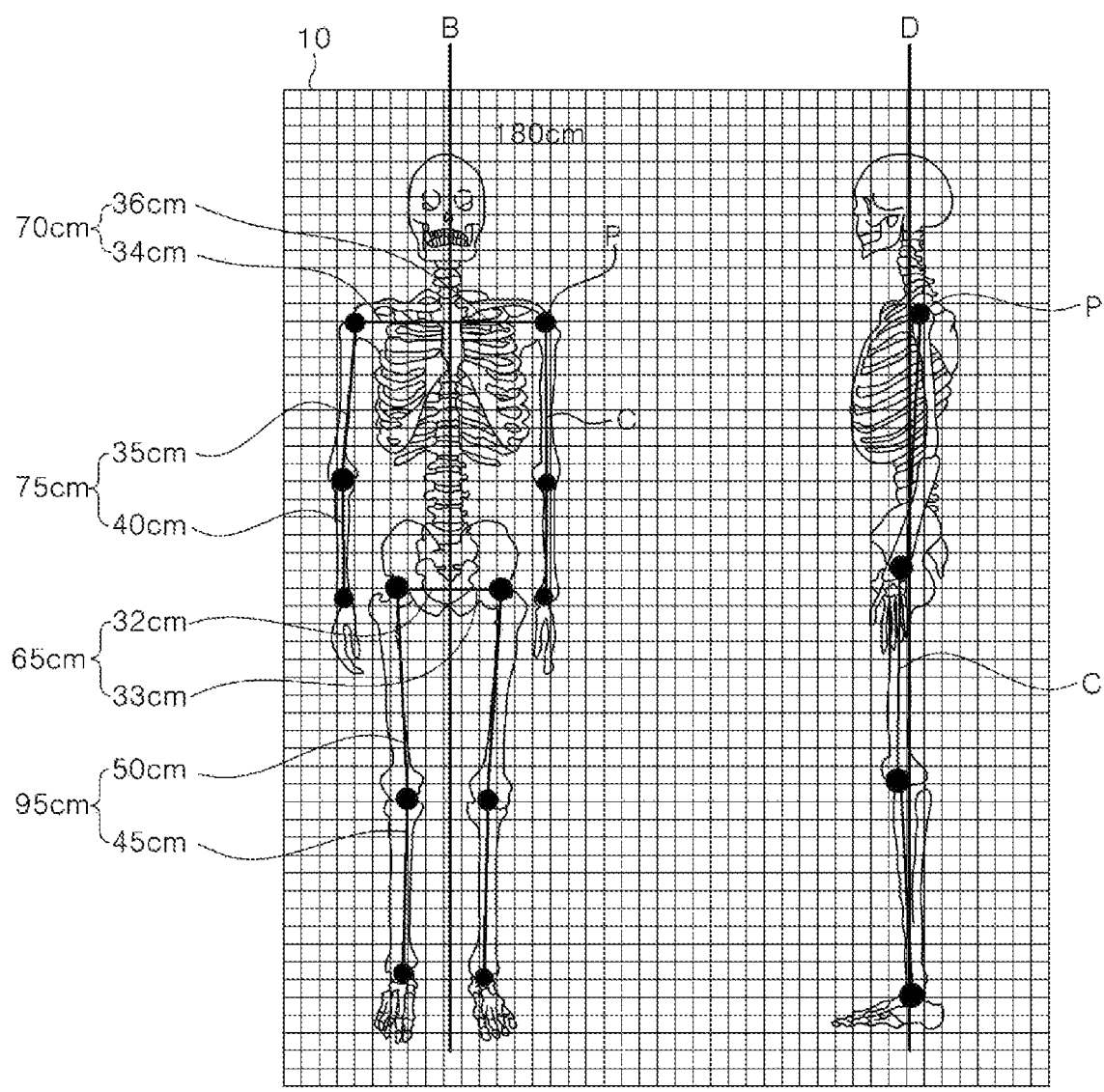
FIG. 2 is a view illustrating a skeleton image generated via image processing by a three-dimensional (3D) depth camera according to an embodiment of the disclosure.
Figure 3:
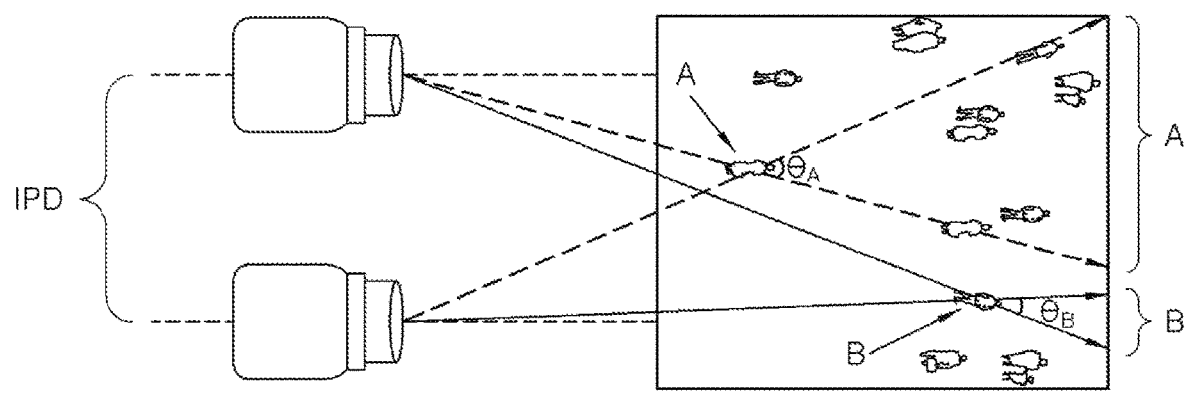
FIG. 3 is a view illustrating a stereo camera method among methods using a three-dimensional (3D) depth camera according to an embodiment of the disclosure.
Figure 4:
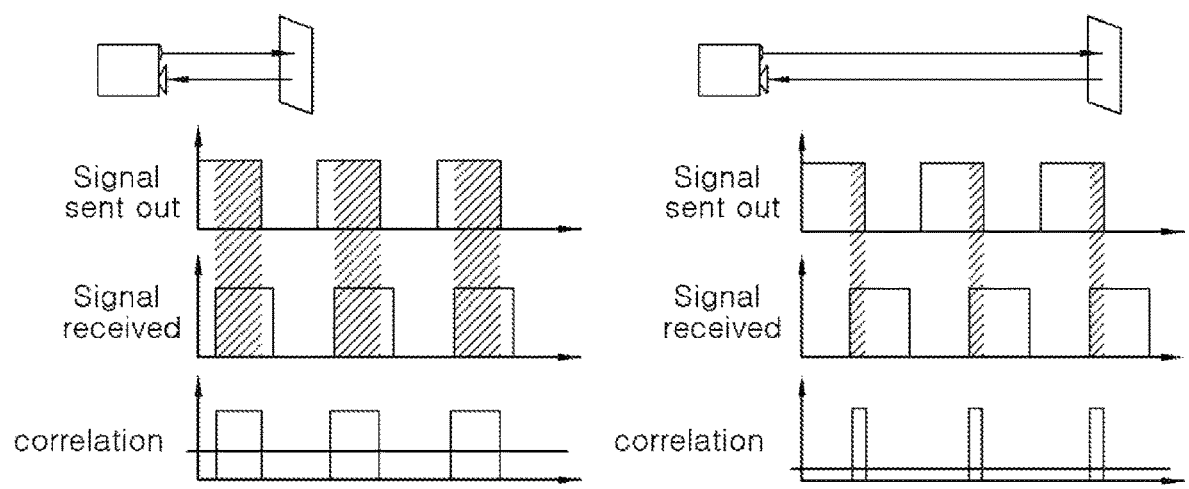
FIG. 4 is a view illustrating a time-of-flight (ToF) method among methods using a three-dimensional (3D) depth camera according to an embodiment of the disclosure.
Figure 5:
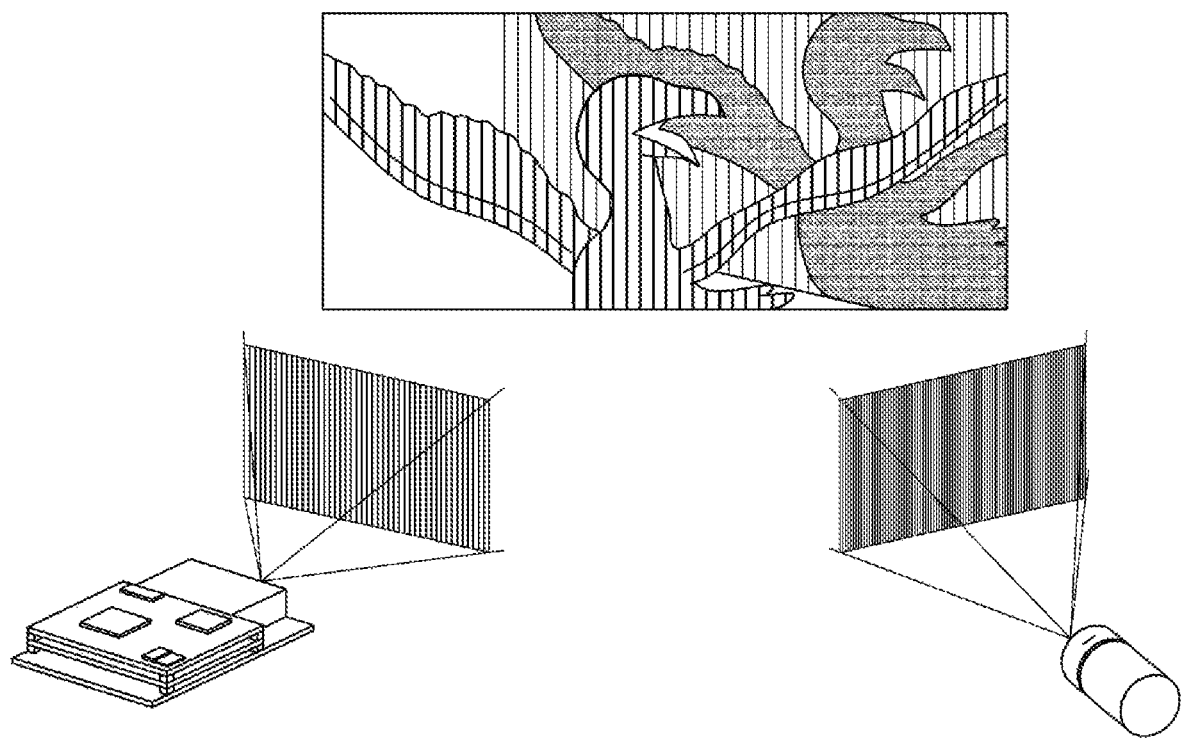
FIG. 5 is a view illustrating a structured pattern method among methods using a three-dimensional (3D) depth camera according to an embodiment of the disclosure.
Figure 6:
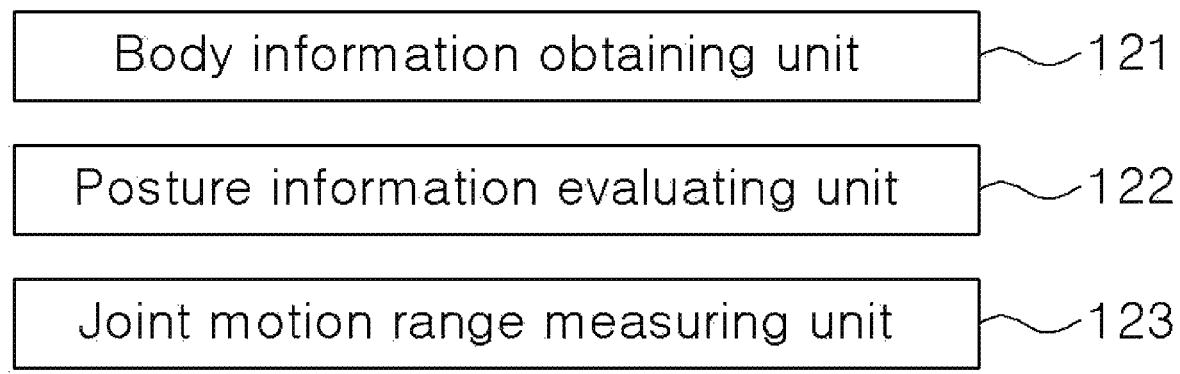
FIG. 6 is a block diagram illustrating a configuration of an information processor according to an embodiment of the disclosure.
Figure 7:
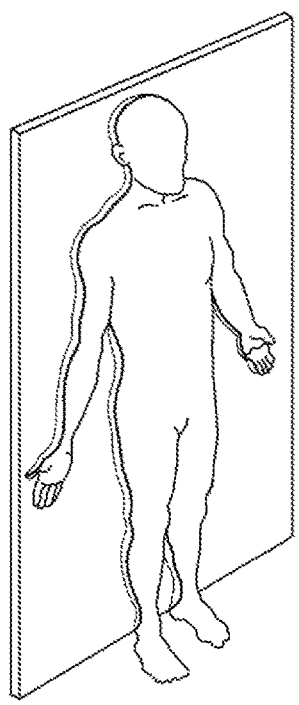
FIG. 7 is a view illustrating three surfaces of a human body for measuring a motion of a body joint according to an embodiment of the disclosure.
Figure 7:
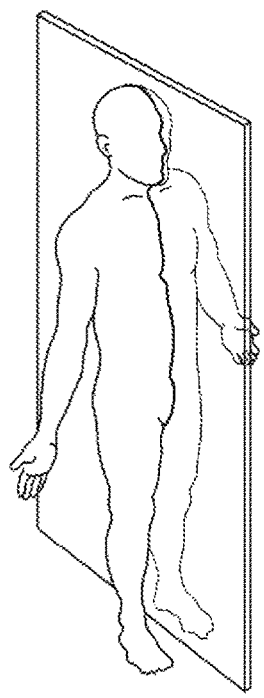
Figure 7:
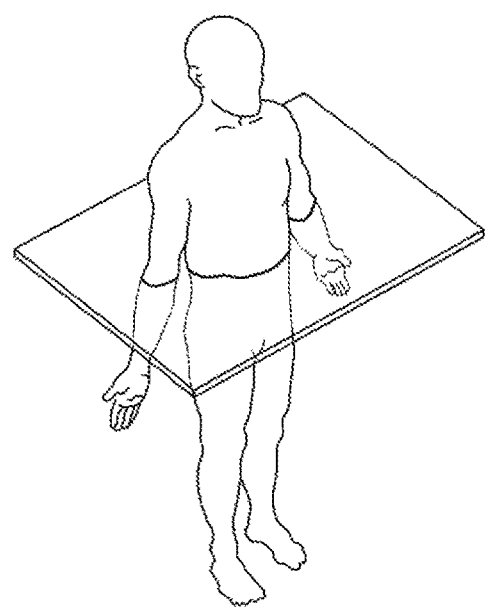
Figure 8:
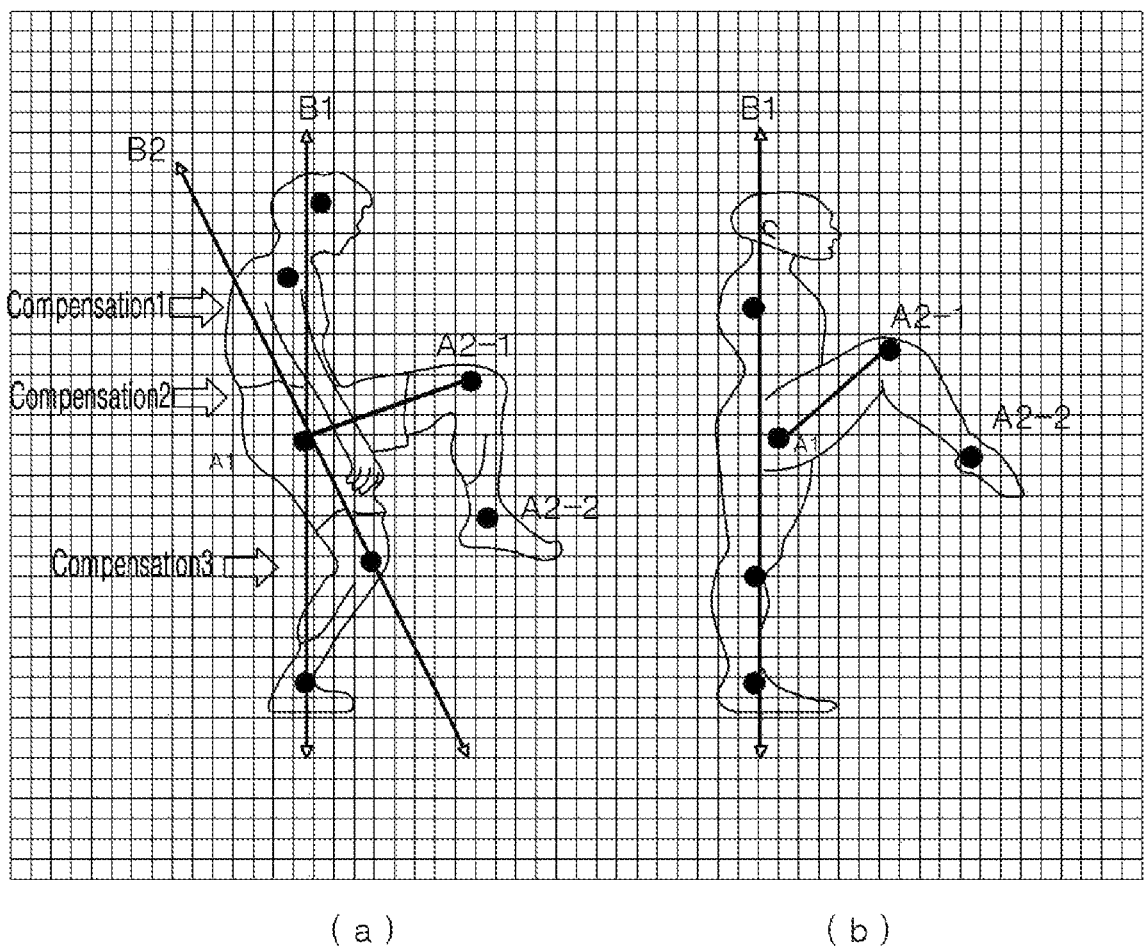
FIG. 8 is a view illustrating an example of measuring a hip joint motion range according to an embodiment of the disclosure.
Figure 9:
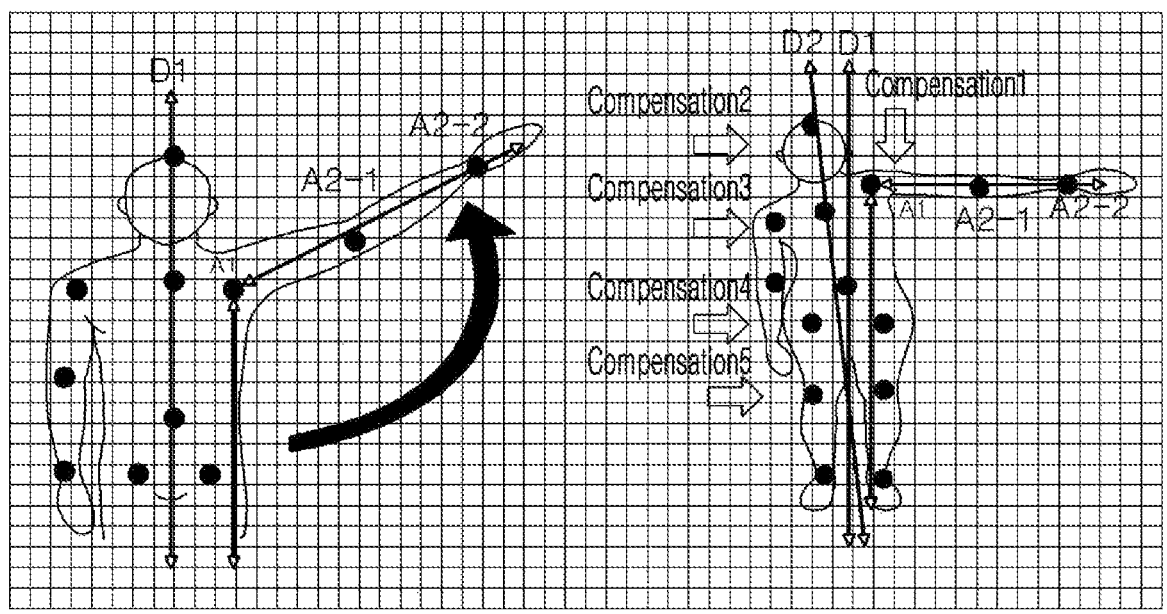
FIG. 9 is a view illustrating an example of measuring a shoulder joint motion range according to an embodiment of the disclosure.

FIG. 1 is a block diagram illustrating an overall configuration of an exercise feedback system via measurement of body information, posture information, and joint motion range according to an embodiment of the disclosure. FIG. 2 is a view illustrating a skeleton image generated via image processing by a three-dimensional (3D) depth camera according to an embodiment of the disclosure. FIG. 3 is a view illustrating a stereo camera method among methods using a three-dimensional (3D) depth camera according to an embodiment of the disclosure. FIG. 4 is a view illustrating a time-of-flight (ToF) method among methods using a three-dimensional (3D) depth camera according to an embodiment of the disclosure. FIG. 5 is a view illustrating a structured pattern method among methods using a three-dimensional (3D) depth camera according to an embodiment of the disclosure. FIG. 6 is a block diagram illustrating a configuration of an information processor according to an embodiment of the disclosure. FIG. 7 is a view illustrating three surfaces of a human body for measuring a motion of a body joint according to an embodiment of the disclosure. FIG. 8 is a view illustrating an example of measuring a hip joint motion range according to an embodiment of the disclosure. FIG. 9 is a view illustrating an example of measuring a shoulder joint motion range according to an embodiment of the disclosure.

Referring to FIG. 1, according to an embodiment, an exercise feedback system 100 via measurement of body information, posture information, and joint motion range includes a target image display 110, an information processor 120, and an exercise feedback provider 130. The target image display 110, the information processor 120, and the exercise feedback provider 130 may be, or may be implemented as, or may include, a circuit (or circuitry) for performing its operations or functions described herein.

The target image display 110 may form a skeleton image of a target person on a grid pattern 10 having a predetermined unit length and coordinates, as shown in FIG. 2, via image processing by a three-dimensional (3D) depth camera. Since the 3D depth camera may obtain a desired image when the subject moves, the target person may be guided to follow specific movements while monitoring the specific movements.

According to an embodiment, the 3D depth camera may be implemented with several cameras which may be installed on the front or sides or top, or the 3D depth camera may be implemented as a single camera that measures the target person while the target person moves.

For example, the 3D depth camera applied to the target image display 110 may be implemented as stereo cameras as shown in FIG. 3, a time-of-flight (ToF) camera as shown in FIG. 4, or a structured pattern camera as shown in FIG. 5. For example, Kinect, light detection and ranging (LiDAR), laser detection and ranging (Ladar), time-of-flight (ToF), laser scanner, or laser radar which may be applied to the 3D depth camera, may adopt a sensing scheme of detecting an object and mapping with distance and may emit light pulses to the target and measure the characteristics of the signal reflected by the target. In this case, the width of the light pulse may be varied from nano seconds to micro seconds.

Referring to FIG. 3, the stereo camera method generates a stereoscopic image using two two-dimensional (2D) image sensors and adopts a common 3D depth recognition sensor scheme. To measure the distance from the target person, the stereo camera method uses the viewpoint discrepancy between a pair of same cameras. In this approach, the gaze centers of the two cameras are separated by a base line or inter-pupillary distance (IPD) to create the parallax required for depth measurement, and in general, the optical axes of the cameras may be parallel to each other and perpendicular to a plane with a sense of perspective. For the distance from the given subject, that is, the target person, the IPD determines the angle θ of the subject as seen by the camera pair, and thus plays an important role in detecting parallax. It enables more effective depth discrimination, defines an operating range, and affects the depth resolution limit at various subject distances.

Referring to FIG. 4, the ToF method obtains the movement time information by measuring a delay or a phase shift of a modulated optical signal for all pixels constituting a scene. In general, the optical signal is located in the near-infrared part of the spectrum not to interfere with human vision, and the ToF sensor is composed of a pixel array that allows each pixel to determine the distance to the scene. Further, each pixel measures the delay of the received optical signal with respect to the transmitted signal, and a correlation function is performed on each pixel, and averaging or integration is performed. The resulting correlation value represents the travel time or delay. Further, the TOF method calculates the depth of field and implements 3D by measuring the time taken for light, such as infrared light, to reach the subject and return. Such ToF method has advantages in light of measurement distance and may recognize a human or thing that is far away.

Referring to FIG. 5, the structured pattern method is an optical 3D scanning method that projects a structured set of light patterns to the target and capture the resultant image using an image sensor. The structured light replaces the second image sensor of the stereoscopic vision sensor with a projection component. Like stereoscopic vision techniques, this approach uses the separation between the camera and the projection device to find a specific point and uses a triangulation algorithm to calculate the depth. Image processing and the triangulation algorithm transform the distortion of the projected pattern due to surface roughness into 3D information.

Before measuring the body information, posture information, and joint motion range, the target image display 110 may specify a plurality of feature points P corresponding to the target person's joints, reference points corresponding to measurement targets, among the feature points P, and motion points corresponding to joints moving with respect to each reference point and connection lines C connecting the feature points P as shown in FIG. 2. In other words, after generating the feature points P, the target image display 110 may generate the connection lines based on the generated feature points P and specify reference points and motion points upon measuring the joint motion range, among the feature points P.

According to an embodiment, the feature point P may mean each joint point in the skeleton image. Upon measuring the joint motion range, the feature point P may become a reference point if it becomes a measurement target and, if the corresponding reference point is specified, the feature point P may be specified as a motion point corresponding to a joint moved with respect to the reference point. The connection line C is a line connecting adjacent joints and may be a virtual line connecting the arm joints, the shoulders connecting the arms, the leg joints, the leg joint and the hip joint, and the hip joints.

The information processor 120 uses the feature points P, connection lines C, grid pattern 10, and human body gravity line B and median line D specified through the target image display 110, obtaining or producing various body information, evaluating the posture information according to preset posture classification criteria, and tracking the motion of the motion point with respect to the reference point to thereby measure the joint motion range.

To that end, the information processor 120 may include a body information obtaining unit 121, a posture information evaluating unit 122, and a joint motion range measuring unit 123 as shown in FIG. 6. Each of the body information obtaining unit 121, the posture information evaluating unit 122, and the joint motion range measuring unit 123 may be, or may be implemented as, or may include, a circuit (or circuitry) for performing its operations or functions described herein.

The body information obtaining unit 121 may obtain or produce body information, including left-right symmetry information and physical numerical information for the target person's height, angle, area, or ratio, from the skeleton image, using the feature points P, connection lines C, grid pattern 10, human body gravity line B and median line D.

Here, the center of gravity of the human body is a point above the center line just in front of the level of the second sacrum. The line of gravity of the human body means a virtual vertical line passing through the center of gravity. The line of gravity is a vertical line passing through the center of gravity. The line of gravity acting on a person standing in an ideal position passes the mastoid process, the front of the second sacral vertebra, just behind the hip joint, and before the knee joint, ankle joint, or the talocrural joint. Human postures are classified according to the type of spine, and the human spine has spinal curves in order to show optimal efficiency against gravity. Spinal curvature has lordosis in the cervical spine, kyphosis in the thoracic spine, lordosis in the lumbar spine, and kyphosis in the sacrum.

However, abnormal postures are classified according to the changes in the curvature of the spine. The following shows the posture according to the curvature of the spine, which may be measured using the median line when viewed from the side. The gravity line passing behind the waist creates an extension torque in the waist, forming a natural lordosis curve, and the gravity passing the front of the waist creates a constant bending torque. This is the cause of an abnormal posture.

Abnormal spinal curvature caused by external torque may change the relationship between the gravity line and each vertebral region, causing a decrease in motor performance and injury, and damage due to increased stress in muscles, ligaments, bones, spinal discs, protrusion joints, and spinal nerve roots.

In this embodiment, asymmetry between the front and rear joints or between the left and right joints may be measured in a posture and during exercise using the gravity line B and the median line D dividing the human body to the left and right, and the gravity line B may be used mainly to determine the body posture information.

The length of the body segment may be measured using the gravity line B and the median line D, as well as the feature points P, the connection lines C, and the grid pattern 10 of the skeleton image generated by the 3D depth camera, and asymmetry may be identified by comparing the measured lengths and heights of the left and right body segments.

The body information measured in this embodiment may include the height (leg length, torso length) and head position, neck length, shoulder and chest widths, abdomen and pelvis widths, neck and torso lengths, upper arm and forearm lengths and arm length, thigh and lower leg lengths, or other body lengths, and the Q-angle. These physical values may be expressed in length (cm), angle (°), area (cm$^2$), and ratio (%). Upon measuring the joint motion range, the movement of each connecting point or whether it moves may be observed based on the body length information.

The effect of the asymmetry between the body lengths measured in this embodiment on the human body during exercise is described below with examples of squat and shoulder press which are multi joint exercise. The difference between the thigh and lower leg which are different in length during multi joint exercise (squat) causes different loads to be applied to the hip, knee and ankle joints during the squat exercise. This indicates that different muscular strengths and degrees of flexibility are required on both sides. If a person with the same height but different lengths of body parts performs a squat, with the center of weight aligned with the body's gravitational line, considering only stability, stress or development may be caused on different muscles and joints, resulting in joint asymmetry.

During a shoulder press, which is a representative shoulder exercise of the upper body, different loads are applied to the left arm and the right arm due to the difference between the heights of the shoulders or between the lengths of the arms. As such, different lengths or asymmetry of the body acts as an abnormal stress on the body and causes different forms of development, which in turn causes problems in the joints, resulting in an asymmetrical joint motion range.

Accordingly, according to an embodiment, in order to optimize the stress applied to the body due to the different limb lengths, the optimal exercise may be fed back through length evaluation of the body segments.

The posture information evaluating unit 122 may obtain (or produce) and evaluate the posture information for the target person according to posture classification criteria preset from the skeleton image using the gravity line B and the median line D.

The skeleton of the human body is supported and moved by the muscles of the body and, when the muscles are under- or over-loaded, or function abnormally, the posture may be misaligned. This muscle imbalance makes the body vulnerable to injuries, tension, and pain. If not used for a long time, the muscles that maintain the posture may become weak, tense or be painful. Repetitive movements may cause muscle imbalance, resulting in dysfunction and compensation.

Ideally, the body needs balanced activities to develop postural strength and endurance. A correct posture may advantageously keep the body in the optimal posture to reduce the risk of injury and pain in everyday activities, as well as correct movement of joints, ligaments and muscles. Further, the correct posture allows for the distribution of weight so that certain parts of the body are not overused or compensated. This enables the body posture to be efficiently maintained with the minimum loads in the optimal alignment. This allows for efficient movements.

The gravity line B and median line D are accurate criteria for posture evaluation, which is a static assessment of the body. For posture evaluation, postures are measured and classified using the grid pattern 10, gravity line B, and median line D. The movement of the extended connection point, or whether it is moved, based on the pre-measured posture evaluation information upon measuring the joint motion range may be observed.

The reason for measuring the joint motion range after performing the posture evaluation in this embodiment is that the joint motion range of shoulder abduction may be reduced due to, e.g., the sway back posture or turtle neck posture and, thus, to accurately measure the joint motion range, it may be necessary to determine the correlation or relationship between the target person's posture and the joint motion range through an accurate posture evaluation.

According to an embodiment, the posture information may be largely classified into four types: ideal posture, sway back posture, flat back posture, and kyphotic lordotic posture.

In the ideal posture, the head may be neutral in position, the cervical spine normally curved, the thoracic spine normally curved and slightly posteriorly convex, the lumbar spine normally curved, the pelvis neutral, the anterior superior iliac spine and pubic symphysis positioned on a vertical line, and the hip, knee, and ankle joints neutral. In the ideal posture, the spine is normally curved (cervical lordosis, thoracic kyphosis, lumbar lordosis), and the pelvis and lower limb joints remain neutral without being bent or stretched.

In the sway back posture, the head is positioned forward, the cervical spine is slightly extended, the thoracic spine has increased flexion (long kyphosis) with a posterior displacement of the upper trunk, the lumbar has flexion (flattening) of the lower lumbar area, the pelvis is posteriorly tilted, the hip joints have hyper extended anterior displacement of the pelvis, the knee joints are hyperextended, and the ankle joints are neutral in position. By the nature of the muscles, one-hip joint flexor, external oblique, upper back extensor, and neck flexor muscles are stretched and weakened, and the hamstrings and upper fibers of the internal oblique muscles are shortened and strengthened.

In the sway back posture, excessive thoracic kyphosis occurs, and the pelvis is moved ahead of the center line of the body, resulting in a posterior slope. Further, the butt is positioned ahead of the head and torso, and the center of gravity is positioned behind the hip joints, so that the knee joints are excessively extended.

In the flat back posture, the head is positioned forward, the cervical spine is slightly extended, the thoracic spine has an increased flexion in its upper part, with the lower part straight, the lumbar is flexed (or straight), the pelvis is posteriorly tilted, the hip joints are extended, the knee joints are extended, and the ankle joints have a slightly plantar flexion. By the nature of the muscles, one-joint hip flexor muscles are stretched and weakened, and hamstrings are shortened and strengthened.

In the kyphoticlodotic posture, the head is positioned forward, the cervical spine is hyperextended, the scapula is abducted, the upper part of the thoracic spine has an increased flexion (kyphosis), the pelvis is anteriorly tilted, hip joints are flexed, knee joints are slightly extended, and ankle joints have a slightly plantar flexion since the lower legs are inclined backwards. By the nature of the muscles, the neck flexor, upper back elector spinae, external oblique, and hamstring muscles are stretched and weakened, and the neck extensor, hip flexor, and lower back muscles are shortened and strengthened. In this kyphoticlodotic posture, the pelvis is inclined forwards (in contrast, in the sway back posture, the pelvis moves forward), and the waist has excessive lordosis, thus, the center of gravity moves forward, so it moves backward in the thoracic spine.

The reason for performing posture classification via the posture evaluation is as follows, according to an embodiment.

The skeleton is supported and moved by body muscles. A posture misalignment may occur when the muscles of the human body are under- or over-loaded, or function abnormally. This muscle imbalance makes the body vulnerable to injuries, tension, and pain. If not used for a long time, the muscles that maintain the posture may become weak, tense or be painful. Repetitive movements may cause muscle imbalance, resulting in dysfunction and compensation. Ideally, the body needs balanced activities to develop postural strength and endurance.

A correct posture may advantageously keep the body in the optimal posture to reduce the risk of injury and pain in everyday activities, as well as correct movement of joints, ligaments and muscles. Further, the correct posture allows for the distribution of weight so that certain parts of the body are not overused or compensated. This enables the body posture to be efficiently maintained with the minimum loads in the optimal alignment. This allows for efficient movements.

The human body's gravitational line and median line are correct standards or references for posture evaluation, which is a static evaluation of the body. For more precise posture evaluation, postures are measured and classified using the grid pattern 10, gravity line B, and median line D. The movement of the extended connection point, or whether it is moved, based on the pre-measured posture evaluation information upon measuring the joint motion range may be observed.

The reason for measuring the joint motion range after performing the posture evaluation in this embodiment is that the joint motion range of shoulder abduction may be reduced due to, e.g., the sway back posture or turtle neck posture. Therefore, to accurately measure the joint motion range, it may be necessary to determine the correlation or relationship between the target person's posture and the joint motion range through an accurate posture evaluation The joint motion range measuring unit 123 may measure the joint motion range by tracking the motion of the motion points with respect to the reference points, and may remeasure the joint motion range by sensing the motion of the feature points except for the reference points and the motion points or exclude the angle of motion of the motion points from the measured joint motion range to thereby enable more accurate measurement. The reference points may be joint points subject to measurement among the feature points, and the motion points may be joint points which correspond to the joints moved with respect to the reference points.

In general, the joint motion range means a range in which the joint moves and is influenced by the flexibility of the muscle. In the human body, joints and muscles play complementary roles in order to generate movement. as one organism. Therefore, when the body moves, an abnormal movement occurs in an adjacent joint or muscle due to inconsistent movement or restrictions on the joint, or lack of flexibility of the muscle, and continuous increase in stress may cause asymmetry of the body.

A normal joint motion range (joint motion range is also referred to as range of motion (ROM)) may be divided into an active ROM and a passive ROM. The passive ROM may be assessed or evaluated while the measurer passively helps the customer or patient moving their joints). The active ROM may be assessed or evaluated as a motion range which may be created by the customer's or patient's own power. By such evaluation or assessment, a limit of motion (LOM) of the joint (which may simply be referred to as joint LOM) may be obtained. As such, the joint motion range is divided into the passive ROM and the active ROM depending on whether the subject or target person (e.g., the above-mentioned customer or patient) moves with the aid of others or on their own power.

For each body joint, a normal angle is determined. When a joint is moved at an angle smaller than the normal angle determined therefor, the joint may be defined as rigid or hypomobile and as being at higher risk of injury upon body activity. If a joint moves at an angle larger than its normal angle, the joint may be put at higher risk of injury and exhibit hyper extension or hypermobile characteristics as compared with the normal joint. Upon exercise requiring movement of the entire body (e.g., simple-joint, or multi joint exercise, or golf), the joints with insufficient movement and the joints with excessive movement may influence the motion of normal joints, cause injury, or negatively affect athletic performance.

Limited joint movements may be regarded as normal due to the compensation. The movement of a body portion (joint or muscle) where compensation occurs may cause repetitive damage and resultantly a limitation on the joint motion range upon exercise. In order to address these issues, it may be important to restore the limited joint function (joint motion range or flexibility of the associated muscles) by measuring the normal motion of the joint in the joint motion range or by identifying the compensation of the adjacent body portion (joint or muscle).

Therefore, according to an embodiment, it is possible to measure the range of motion of each joint of the body and divide into hypomobile, hypermobile, and normal motion, to previously determine and compensate for the influence of the posture and body symmetry on the joint motion range, and to measure the compensation occurring from other joints or muscles upon measurement, thereby allowing for more reliable measurement of the joint motion range.

Conventional joint motion range measurement methods may measure only the motion rage of each joint. However, the range of motion of the joint is reduced due to abnormal movements, injuries or absence of rehabilitation after surgery, or repetitive damage, or in the case of multi-directional motion joints (shoulder, hip, or ankle joints), the movement of one side is restricted. As such, in the case of a joint with a limited range of motion, a compensation action occurs in the adjacent joint due to the disharmony of motion, and the compensation action may cause the measurement range to be regarded as a normal angle.

The conventional joint motion range measurement methods fail to perform correct measurement because they do not take into account the occurrence of compensatory movements in body parts (joints) other than the joint under measurement.

According to an embodiment, it is possible to provide an accurate joint motion range by measuring complementary movements in other body parts (muscles or joints) than the joint being measured. To that end, reference points and motion points are selected or determined from among the feature points P of the body joints using the grid pattern P, gravity line B, and median line D, it is identified whether the reference point is moved or whether the gravity line or median line is moved, and if a movement occurs in a joint other than the joint being measured, it may be recognized as the body's compensation.

As the movements occurring in the body joints, movements may occur on the sagittal plane, frontal plane, and horizontal plane as shown in FIG. 7. Flexion and extension may occur on the sagittal plane, abduction and adduction may occur on the frontal plane, and rotation and rotational motion which are complex motion can occur on the horizontal plane. For the motion on the sagittal plane, the joint motion range on a side surface of the body may be measured using the gravity line, and the motion on the frontal plane may be measured using the median line, and the motion on the horizontal plane may be measured using the gravity line and the median line.

According to an embodiment, the joint motion range measuring unit 123 may measure the joint motion range using the three methods. Hereinafter, the above-described three methods may be referred to as a first measurement method, a second measurement method, and a third measurement method for ease of description.

Referring to FIG. 8, the first measurement method for measuring the hip joint motion range is described.

Image processing by the 3D depth camera is used to generate a skeleton image for the target person on the grid pattern 10, specify the feature point P on each joint, specify a reference point A1 and a motion point A2-1 as shown in FIG. 8, identify connection points extended (adjacent) and connected from the joint subjected to measurement, identify and evaluate the length information and posture classification of each body part using the gravity line B1, and then measure the joint motion range for the hip joint.

Upon sensing at least one of the movement of a first connection point except for the motion point A2-1, extended and connected via each connection line from the reference point A1 among the feature points P, and the movement of the gravity line B1 or median line (not shown), the joint motion range may be remeasured.

Upon measuring the range of motion of the flexion of the hip joint, the gravity line B1 is used for measurement and evaluation of the normal joint motion range, and motion on sagittal plane is evaluated. At this time, the normal hip joint motion range is about 125 degrees.

However, a motion occurs in the first connection point (right knee joint and spinal joint) connected and extended from the reference point A1 of the hip joint upon measurement of the hip joint motion range shown in (a) of FIG. 8 and, thus, the joint motion range may be remeasured.

As such, the first cause of the compensation action upon measuring the hip joint motion range is presumed to be weakened hip flexor muscle strength or insufficient flexibility of the biceps femoris and gluteus maximus and microdamage, asymmetry, imbalance, and adhesion of the joint.

The second measurement method for measuring the hip joint motion range is described below.

In the second measurement method, in the case of sensing the movement of the second connection point adjacent to the reference point A1 and connected via the connection line from the reference point A1 among the feature points P upon measuring the joint motion range, the joint motion range may be measured by calculating a first angle generated by the movement of the motion point A2-1 and a second angle generated by the movement of the second connection point and subtracting the second angle from the first angle.

More specifically, although a movement of about 110 degrees occurs at the reference point A1 and motion point A2-1 as in the hip joint flexion as shown in FIG. 8(*a*) and is so shown as if a normal hip joint motion range has been measured, the compensational angle by the gravity line B1 of the body and the gravity line B2 formed as the gravity line B1 moves needs to be excluded from the angles of the reference point A1 and the motion point A2-1 to precisely calculate the range of motion angle of the hip joint flexion shown in FIG. 8(*b*).

As such, the second cause of the occurrence of the compensational action upon measuring the hip joint motion range is presumed to be an increase in the motion range due to a bent back that is caused by the contraction of the upper rectus abdominis and resultant flexion compensation of the spine.

In the third measurement method, the joint motion range may be remeasured in the case of sensing a movement of the third connection point A2-2 which corresponds to the limb end joint adjacent to the motion point A2-1 and connected via the connection line from the reference point A1 among the feature points.

More specifically, the joint motion range of hip joint flexion may be obtained by measuring the motion point A2-1 of the joint (knee) adjacent to the reference point A1, but the joint motion range is presumed to have increased due to the movement of the third connection point A2-2 (ankle dorsiflexion) which is the limb end joint point connected with the motion point A2-1, and because this is not the correct measurement of the joint motion range of the hip joint flexion, remeasurement may be performed.

Referring to FIG. 9, the first measurement method for measuring the shoulder joint motion range is described.

As shown in (a) of FIG. 9, for evaluation of measurement of the normal motion range upon measuring the shoulder joint abduction motion range, the median line D1 on the front may be used, and motion on the frontal plane may be evaluated. At this time, the normal motion range of the shoulder joint is about 180 degrees.

However, as an actual result of measurement, a motion occurs due to an elevation of the reference point A1 by the trapezius (compensation 1) extended and connected from the reference point A1 which is a should joint reference point and movement, to D2, of the median line D1, which is the central axis of the body, and thus, remeasurement may be performed.

As such, the first cause of the elevation compensation of the scapula when measuring the range of motion of the shoulder joint is presumed to be weakened shoulder abductor muscle or insufficient flexibility of the lats, and microdamage, asymmetry, imbalance, or adhesion the joint and resultant contraction of the trapezius muscle.

The second measurement method for measuring the shoulder joint motion range is described below.

In the shoulder abduction as shown in (b) of FIG. 9, the reference point A1 and the motion point A2 are shown as if they have been moved at 90 degrees with respect to the median line D1. However, for the actual angle at which the movement has occurred in the shoulder, the abduction joint motion range of the left shoulder, i.e., the actual motion range for the reference point A1 and the motion point A2-1 and the shoulder joint motion range according thereto may be precisely measured by excluding the angle between the median line D1 of the body and D2 formed as the median line is moved from the angle of the reference point A1 and the motion point A2-1.

The second cause of the compensation upon measuring the shoulder joint motion range is presumed to be movement of the center of body by the insufficient shoulder abduction.

The third measurement method for measuring the shoulder joint motion range is described below.

As shown in (a) of FIG. 9, the accurate joint motion range for the shoulder abduction requires the motion point A2-1 of the joint (elbow) adjacent to the reference point A1. However, the join request message seems to have increased due to the movement (flexion of elbow) of the connection point A2-2 which is the limb end joint point connected with the motion point A2-1 and, because this is precise measurement of the shoulder joint motion range, remeasurement may be performed.

The third cause of the compensation upon measuring the shoulder joint motion range is presumed to be body asymmetry caused by the movement of the connection point A2-2 which is the limb end for helping the reduced joint motion range.

The exercise feedback provider 130 may provide exercise recommendation information based on the measured body information, posture information, and joint motion range.

According to an embodiment, exercise feedback performs exercise on the low motion joint according to the motion range or the hyper motion range joint is provided according to the motion range of the normal joint. As such, exercise needs to be done according to the normal motion range criteria to reduce injury or pain. In the case of hypermobility, the loosened joint may be stabilized, and in the case of hypomobility, the stiff joint may turn mobile.

Upon doing complex joint exercise including motion of one or more joints, the joint motion range needs to have the mobility in the normal range. For example, during a squat exercise, three joints, including the hip joint, knee joint, and ankle joint, move. When performing a squat exercise, if one of the three joints has 70% mobility and the other two joints have 100% mobility, and the exercise is performed in a range of motion greater than 70%, then the joint with 70% mobility, as well as left-right symmetry, may be subjected to abnormal stress.

As a solution to this, according to an embodiment, the optimal exercise information for safely doing exercise may be fed back by identifying and evaluating the body information and the posture information before doing exercise, identifying asymmetry of the joint motion range by measuring a more precise joint motion range considering, e.g., compensation action upon measurement, and performing exercise on the low motion joint according to the motion range.

Figure 10:
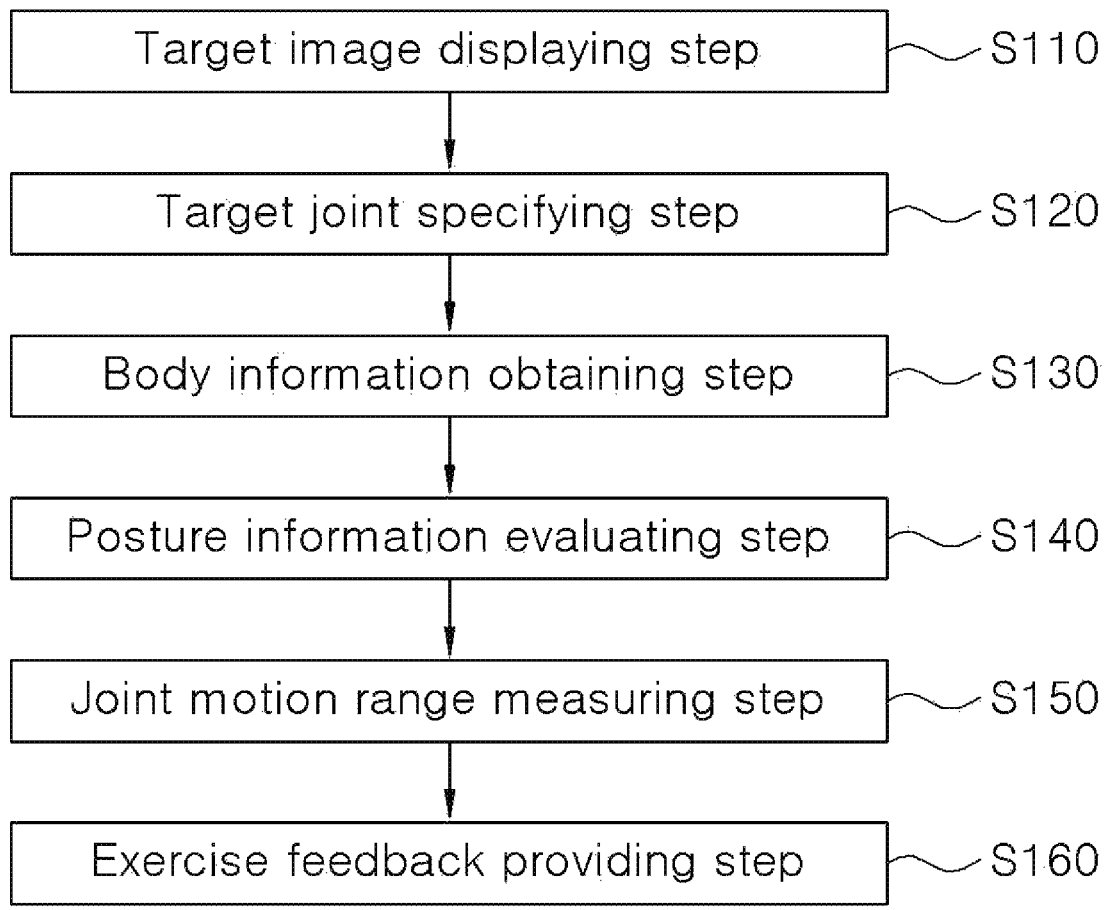
FIG. 10 is a flowchart illustrating an exercise feedback method via measurement of body information, posture information, and joint motion range according to an embodiment of the disclosure.

FIG. 10 is a flowchart illustrating an exercise feedback method via measurement of body information, posture information, and joint motion range according to an embodiment of the disclosure.

Referring to FIG. 10, according to an embodiment, an exercise feedback method S100 via measurement of body information, posture information, and joint motion range regards a method for providing the optimal exercise feedback information using the above-described exercise feedback system 100 and includes a target image displaying step S110, a target joint specifying step S120, a body information obtaining step S130, a posture information evaluating step S140, a joint motion range measuring step S150, and an exercise feedback providing step S160.

In the target image displaying step S110, a skeleton image of a target person may be formed on a grid pattern 10 having a predetermined unit length and coordinates, as shown in FIG. 2, via image processing by a three-dimensional (3D) depth camera.

According to an embodiment, the 3D depth camera may be implemented with several cameras which may be installed on the front or sides or top, or the 3D depth camera may be implemented as a single camera that measures the target person while the target person moves.

For example, the 3D depth camera applied to the target image display 110 may be implemented as stereo cameras as shown in FIG. 3, a time-of-flight (ToF) camera as shown in FIG. 4, or a structured pattern camera as shown in FIG. 5.

Referring to FIG. 3, the stereo camera method generates a stereoscopic image using two two-dimensional (2D) image sensors and adopts a common 3D depth recognition sensor scheme. To measure the distance from the target person, the stereo camera method uses the viewpoint discrepancy between a pair of same cameras. In this approach, the gaze centers of the two cameras are separated by a base line or inter-pupillary distance (IPD) to create the parallax required for depth measurement, and in general, the optical axes of the cameras may be parallel to each other and perpendicular to a plane with a sense of perspective. For the distance from the given subject, that is, the target person, the IPD determines the angle θ of the subject as seen by the camera pair, and thus plays an important role in detecting parallax. It enables more effective depth discrimination, defines an operating range, and affects the depth resolution limit at various subject distances.

Referring to FIG. 4, the ToF method obtains the movement time information by measuring a delay or a phase shift of a modulated optical signal for all pixels constituting a scene. In general, the optical signal is located in the near-infrared part of the spectrum not to interfere with human vision, and the ToF sensor is composed of a pixel array that allows each pixel to determine the distance to the scene. Further, each pixel measures the delay of the received optical signal with respect to the transmitted signal, and a correlation function is performed on each pixel, and averaging or integration is performed. The resulting correlation value represents the travel time or delay.

Referring to FIG. 5, the structured pattern method is an optical 3D scanning method that projects a structured set of light patterns to the target and capture the resultant image using an image sensor. The structured light replaces the second image sensor of the stereoscopic vision sensor with a projection component. Like stereoscopic vision techniques, this approach uses the separation between the camera and the projection device to find a specific point and uses a triangulation algorithm to calculate the depth. Image processing and the triangulation algorithm transform the distortion of the projected pattern due to surface roughness into 3D information.

Before measuring the body information, posture information, and joint motion range, the target image display 110 may specify a plurality of feature points P corresponding to the target person's joints, reference points corresponding to measurement targets, among the feature points P, and motion points corresponding to joints moving with respect to each reference point and connection lines C connecting the feature points P as shown in FIG. 2.

According to an embodiment, the feature point P may mean each joint point in the skeleton image. Upon measuring the joint motion range, the feature point P may become a reference point if it becomes a measurement target and, if the corresponding reference point is specified, the feature point P may be specified as a motion point corresponding to a joint moved with respect to the reference point. The connection line C is a line connecting adjacent joints and may be a virtual line connecting the arm joints, the shoulders connecting the arms, the leg joints, the leg joint and the hip joint, and the hip joints.

In the body information obtaining step S130, the posture information evaluating step S140, and the joint motion range measuring step S150, the feature points P, connection lines C, grid pattern 10, and human body gravitational line B and median line D specified by the target image displaying step S110 may be used to obtain or produce various body information, evaluate the posture information according to preset posture classification criteria, and track the motion of the motion point with respect to the reference point to thereby measure the joint motion range.

In the body information obtaining step S130, body information, including left-right symmetry information and physical numerical information for the target person's height, angle, area, or ratio, from the skeleton image, may be obtained or produced using the feature points P, connection lines C, grid pattern 10, human body gravitational line B and median line D.

Here, the center of gravity of the human body is a point above the center line just in front of the level of the second sacrum. The line of gravity of the human body means a virtual vertical line passing through the center of gravity. The line of gravity is a vertical line passing through the center of gravity. The line of gravity acting on a person standing in an ideal position passes the mastoid process, the front of the second sacral vertebra, just behind the hip joint, and before the knee joint, ankle joint, or the talocrural joint. Human postures are classified according to the type of spine, and the human spine has spinal curves in order to show optimal efficiency against gravity. Spinal curvature has lordosis in the cervical spine, kyphosis in the thoracic spine, lordosis in the lumbar spine, and kyphosis in the sacrum.

However, abnormal postures are classified according to the changes in the curvature of the spine. The following shows the posture according to the curvature of the spine, which may be measured using the median line when viewed from the side. The gravity line passing behind the waist creates an extension torque in the waist, forming a natural lordosis curve, and the gravity passing the front of the waist creates a constant bending torque. This is the cause of an abnormal posture.

Abnormal spinal curvature caused by external torque may change the relationship between the gravity line and each vertebral region, causing a decrease in motor performance and injury, and damage due to increased stress in muscles, ligaments, bones, spinal discs, protrusion joints, and spinal nerve roots.

In this embodiment, asymmetry between the front and rear joints or between the left and right joints may be measured in a posture and during exercise using the gravity line B and the median line D dividing the human body to the left and right, and the gravity line B may be used mainly to determine the body posture information.

The length of the body segment may be measured using the gravity line B and the median line D, as well as the feature points P, the connection lines C, and the grid pattern 10 of the skeleton image generated by the 3D depth camera, and asymmetry may be identified by comparing the measured lengths and heights of the left and right body segments.

The body information measured in this embodiment may include the height (leg length, torso length) and head position, neck length, shoulder and chest widths, abdomen and pelvis widths, neck and torso lengths, upper arm and forearm lengths and arm length, thigh and lower leg lengths, or other body lengths, and the Q-angle. These physical values may be expressed in length (cm), angle (°), area (cm$^2$), and ratio (%). Upon measuring the joint motion range, the movement of each connecting point or whether it moves may be observed based on the body length information.

The effect of the asymmetry between the body lengths measured in this embodiment on the human body during exercise is described below with examples of squat and shoulder press which are multi joint exercise. The difference between the thigh and lower leg which are different in length during multi joint exercise (squat) causes different loads to be applied to the hip, knee and ankle joints during the squat exercise. This indicates that different muscular strengths and degrees of flexibility are required on both sides. If a person with the same height but different lengths of body parts performs a squat, with the center of weight aligned with the body's gravitational line, considering only stability, stress or development may be caused on different muscles and joints, resulting in joint asymmetry.

During a shoulder press, which is a representative shoulder exercise of the upper body, different loads are applied to the left arm and the right arm due to the difference between the heights of the shoulders or between the lengths of the arms. As such, different lengths or asymmetry of the body acts as an abnormal stress on the body and causes different forms of development, which in turn causes problems in the joints, resulting in an asymmetrical joint motion range.

Accordingly, according to an embodiment, in order to optimize the stress applied to the body due to the different limb lengths, the optimal exercise may be fed back through length evaluation of the body segments.

In the posture information evaluating step S140, the posture information for the target person may be obtained (or produced) and evaluated according to posture classification criteria preset from the skeleton image using the gravity line B and the median line D.

The skeleton of the human body is supported and moved by the muscles of the body and, when the muscles are under- or over-loaded, or function abnormally, the posture may be misaligned. This muscle imbalance makes the body vulnerable to injuries, tension, and pain. If not used for a long time, the muscles that maintain the posture may become weak, tense or be painful. Repetitive movements may cause muscle imbalance, resulting in dysfunction and compensation.

Ideally, the body needs balanced activities to develop postural strength and endurance. A correct posture may advantageously keep the body in the optimal posture to reduce the risk of injury and pain in everyday activities, as well as correct movement of joints, ligaments and muscles. Further, the correct posture allows for the distribution of weight so that certain parts of the body are not overused or compensated. This enables the body posture to be efficiently maintained with the minimum loads in the optimal alignment. This allows for efficient movements.

The gravity line B and median line D are accurate criteria for posture evaluation, which is a static assessment of the body. For posture evaluation, postures are measured and classified using the grid pattern 10, gravity line B, and median line D. The movement of the extended connection point, or whether it is moved, based on the pre-measured posture evaluation information upon measuring the joint motion range may be observed.

The reason for measuring the joint motion range after performing the posture evaluation in this embodiment is that the joint motion range of shoulder abduction may be reduced due to, e.g., the sway back posture or turtle neck posture and, thus, to accurately measure the joint motion range, it may be necessary to determine the correlation or relationship between the target person's posture and the joint motion range through an accurate posture evaluation.

According to an embodiment, the posture information may be largely classified into four types: ideal posture, sway back posture, flat back posture, and kyphotic lordotic posture.

In the ideal posture, the head may be neutral in position, the cervical spine normally curved, the thoracic spine normally curved and slightly posteriorly convex, the lumbar spine normally curved, the pelvis neutral, the anterior superior iliac spine and pubic symphysis positioned on a vertical line, and the hip, knee, and ankle joints neutral. In the ideal posture, the spine is normally curved (cervical lordosis, thoracic kyphosis, lumbar lordosis), and the pelvis and lower limb joints remain neutral without being bent or stretched.

In the sway back posture, the head is positioned forward, the cervical spine is slightly extended, the thoracic spine has increased flexion (long kyphosis) with a posterior displacement of the upper trunk, the lumbar has flexion (flattening) of the lower lumbar area, the pelvis is posteriorly tilted, the hip joints have hyper extended anterior displacement of the pelvis, the knee joints are hyperextended, and the ankle joints are neutral in position. By the nature of the muscles, one-hip joint flexor, external oblique, upper back extensor, and neck flexor muscles are stretched and weakened, and the hamstrings and upper fibers of the internal oblique muscles are shortened and strengthened.

In the sway back posture, excessive thoracic kyphosis occurs, and the pelvis is moved ahead of the center line of the body, resulting in a posterior slope. Further, the butt is positioned ahead of the head and torso, and the center of gravity is positioned behind the hip joints, so that the knee joints are excessively extended.

In the flat back posture, the head is positioned forward, the cervical spine is slightly extended, the thoracic spine has an increased flexion in its upper part, with the lower part straight, the lumbar is flexed (or straight), the pelvis is posteriorly tilted, the hip joints are extended, the knee joints are extended, and the ankle joints have a slightly plantar flexion. By the nature of the muscles, one-joint hip flexor muscles are stretched and weakened, and hamstrings are shortened and strengthened.

In the kyphoticlodotic posture, the head is positioned forward, the cervical spine is hyperextended, the scapula is abducted, the upper part of the thoracic spine has an increased flexion (kyphosis), the pelvis is anteriorly tilted, hip joints are flexed, knee joints are slightly extended, and ankle joints have a slightly plantar flexion since the lower legs are inclined backwards. By the nature of the muscles, the neck flexor, upper back elector spinae, external oblique, and hamstring muscles are stretched and weakened, and the neck extensor, hip flexor, and lower back muscles are shortened and strengthened. In this kyphoticlodotic posture, the pelvis is inclined forwards (in contrast, in the sway back posture, the pelvis moves forward), and the waist has excessive lordosis, thus, the center of gravity moves forward, so it moves backward in the thoracic spine.

The reason for performing posture classification via the posture evaluation is as follows, according to an embodiment.

The skeleton is supported and moved by body muscles. A posture misalignment may occur when the muscles of the human body are under- or over-loaded, or function abnormally. This muscle imbalance makes the body vulnerable to injuries, tension, and pain. If not used for a long time, the muscles that maintain the posture may become weak, tense or be painful. Repetitive movements may cause muscle imbalance, resulting in dysfunction and compensation. Ideally, the body needs balanced activities to develop postural strength and endurance.

A correct posture may advantageously keep the body in the optimal posture to reduce the risk of injury and pain in everyday activities, as well as correct movement of joints, ligaments and muscles. Further, the correct posture allows for the distribution of weight so that certain parts of the body are not overused or compensated. This enables the body posture to be efficiently maintained with the minimum loads in the optimal alignment. This allows for efficient movements.

The human body's gravitational line and median line are correct standards or references for posture evaluation, which is a static evaluation of the body. For more precise posture evaluation, postures are measured and classified using the grid pattern 10, gravity line B, and median line D. The movement of the extended connection point, or whether it is moved, based on the pre-measured posture evaluation information upon measuring the joint motion range may be observed.

The reason for measuring the joint motion range after performing the posture evaluation in this embodiment is that the joint motion range of shoulder abduction may be reduced due to, e.g., the sway back posture or turtle neck posture. Therefore, to accurately measure the joint motion range, it may be necessary to determine the correlation or relationship between the target person's posture and the joint motion range through an accurate posture evaluation In the joint motion range measuring step S150, the joint motion range may be measured by tracking the motion of the motion points with respect to the reference points, and the joint motion range may be re-measured by sensing the motion of the feature points except for the reference points and the motion points or the angle of motion of the motion points may be excluded from the measured joint motion range to thereby enable more accurate measurement. The reference points may be joint points subject to measurement among the feature points, and the motion points may be joint points which correspond to the joints moved with respect to the reference points.

In general, the joint motion range means a range in which the joint moves and is influenced by the flexibility of the muscle. In the human body, joints and muscles play complementary roles in order to generate movement. as one organism. Therefore, when the body moves, an abnormal movement occurs in an adjacent joint or muscle due to inconsistent movement or restrictions on the joint, or lack of flexibility of the muscle, and continuous increase in stress may cause asymmetry of the body.

A normal joint motion range (joint motion range is also referred to as range of motion (ROM)) may be divided into an active ROM and a passive ROM. The passive ROM may be assessed or evaluated while the measurer passively helps the customer or patient moving their joints). The active ROM may be assessed or evaluated as a motion range which may be created by the customer's or patient's own power. By such evaluation or assessment, a limit of motion (LOM) of the joint (which may simply be referred to as joint LOM) may be obtained. As such, the joint motion range is divided into the passive ROM and the active ROM depending on whether the subject or target person (e.g., the above-mentioned customer or patient) moves with the aid of others or on their own power.

For each body joint, a normal angle is determined. When a joint is moved at an angle smaller than the normal angle determined therefor, the joint may be defined as rigid or hypomobile and as being at higher risk of injury upon body activity. If a joint moves at an angle larger than its normal angle, the joint may be put at higher risk of injury and exhibit hyper extension or hypermobile characteristics as compared with the normal joint. Upon exercise requiring movement of the entire body (e.g., simple-joint, or multi joint exercise, or golf), the joints with insufficient movement and the joints with excessive movement may influence the motion of normal joints, cause injury, or negatively affect athletic performance.

Limited joint movements may be regarded as normal due to the compensation. The movement of a body portion (joint or muscle) where compensation occurs may cause repetitive damage and resultantly a limitation on the joint motion range upon exercise. In order to address these issues, it may be important to restore the limited joint function (joint motion range or flexibility of the associated muscles) by measuring the normal motion of the joint in the joint motion range or by identifying the compensation of the adjacent body portion (joint or muscle).

Therefore, according to an embodiment, it is possible to measure the range of motion of each joint of the body and divide into hypomobile, hypermobile, and normal motion, to previously determine and compensate for the influence of the posture and body symmetry on the joint motion range, and to measure the compensation occurring from other joints or muscles upon measurement, thereby allowing for more reliable measurement of the joint motion range.

Conventional joint motion range measurement methods may measure only the motion rage of each joint. However, the range of motion of the joint is reduced due to abnormal movements, injuries or absence of rehabilitation after surgery, or repetitive damage, or in the case of multi-directional motion joints (shoulder, hip, or ankle joints), the movement of one side is restricted. As such, in the case of a joint with a limited range of motion, a compensation action occurs in the adjacent joint due to the disharmony of motion, and the compensation action may cause the measurement range to be regarded as a normal angle.

The conventional joint motion range measurement methods fail to perform correct measurement because they do not take into account the occurrence of compensatory movements in body parts (joints) other than the joint under measurement.

According to an embodiment, it is possible to provide an accurate joint motion range by measuring complementary movements in other body parts (muscles or joints) than the joint being measured. To that end, reference points and motion points are selected or determined from among the feature points P of the body joints using the grid pattern P, gravity line B, and median line D, it is identified whether the reference point is moved or whether the gravity line or median line is moved, and if a movement occurs in a joint other than the joint being measured, it may be recognized as the body's compensation.

As the movements occurring in the body joints, movements may occur on the sagittal plane, frontal plane, and horizontal plane as shown in FIG. 7. Flexion and extension may occur on the sagittal plane, abduction and adduction may occur on the frontal plane, and rotation and rotational motion which are complex motion can occur on the horizontal plane. For the motion on the sagittal plane, the joint motion range on a side surface of the body may be measured using the gravity line, and the motion on the frontal plane may be measured using the median line, and the motion on the horizontal plane may be measured using the gravity line and the median line.

According to an embodiment, in the joint motion range measuring step S150, the joint motion range may be measured using the three methods. Hereinafter, the above-described three methods may be referred to as a first measurement method, a second measurement method, and a third measurement method for ease of description.

Referring to FIG. 8, the first measurement method for measuring the hip joint motion range is described.

Image processing by the 3D depth camera is used to generate a skeleton image for the target person on the grid pattern 10, specify the feature point P on each joint, specify a reference point A1 and a motion point A2-1 as shown in FIG. 8, identify connection points extended (adjacent) and connected from the joint subjected to measurement, identify and evaluate the length information and posture classification of each body part using the gravity line B1, and then measure the joint motion range for the hip joint.

Upon sensing at least one of the movement of a first connection point except for the motion point A2-1, extended and connected via each connection line from the reference point A1 among the feature points P, and the movement of the gravity line B1 or median line (not shown), the joint motion range may be remeasured.

Upon measuring the range of motion of the flexion of the hip joint, the gravity line B1 is used for measurement and evaluation of the normal joint motion range, and motion on sagittal plane is evaluated. At this time, the normal hip joint motion range is about 125 degrees.

However, a motion occurs in the first connection point (right knee joint and spinal joint) connected and extended from the reference point A1 of the hip joint upon measurement of the hip joint motion range shown in (a) of FIG. 8 and, thus, the joint motion range may be remeasured.

As such, the first cause of the compensation action upon measuring the hip joint motion range is presumed to be weakened hip flexor muscle strength or insufficient flexibility of the biceps femoris and gluteus maximus and microdamage, asymmetry, imbalance, and adhesion of the joint.

The second measurement method for measuring the hip joint motion range is described below.

In the second measurement method, in the case of sensing the movement of the second connection point adjacent to the reference point A1 and connected via the connection line from the reference point A1 among the feature points P upon measuring the joint motion range, the joint motion range may be measured by calculating a first angle generated by the movement of the motion point A2-1 and a second angle generated by the movement of the second connection point and subtracting the second angle from the first angle.

More specifically, although a movement of about 110 degrees occurs at the reference point A1 and motion point A2-1 as in the hip joint flexion as shown in FIG. 8(a) and is so shown as if a normal hip joint motion range has been measured, the compensational angle by the gravity line B1 of the body and the gravity line B2 formed as the gravity line B1 moves needs to be excluded from the angles of the reference point A1 and the motion point A2-1 to precisely calculate the range of motion angle of the hip joint flexion shown in FIG. 8(b).

As such, the second cause of the occurrence of the compensational action upon measuring the hip joint motion range is presumed to be an increase in the motion range due to a bent back that is caused by the contraction of the upper rectus abdominis and resultant flexion compensation of the spine.

In the third measurement method, the joint motion range may be remeasured in the case of sensing a movement of the third connection point A2-2 which corresponds to the limb end joint adjacent to the motion point A2-1 and connected via the connection line from the reference point A1 among the feature points.

More specifically, the joint motion range of hip joint flexion may be obtained by measuring the motion point A2-1 of the joint (knee) adjacent to the reference point A1, but the joint motion range is presumed to have increased due to the movement of the third connection point A2-2 (ankle dorsiflexion) which is the limb end joint point connected with the motion point A2-1, and because this is not the correct measurement of the joint motion range of the hip joint flexion, remeasurement may be performed.

Referring to FIG. 9, the first measurement method for measuring the shoulder joint motion range is described.

As shown in (a) of FIG. 9, for evaluation of measurement of the normal motion range upon measuring the shoulder joint abduction motion range, the median line D1 on the front may be used, and motion on the frontal plane may be evaluated. At this time, the normal motion range of the shoulder joint is about 180 degrees.

However, as an actual result of measurement, a motion occurs due to an elevation of the reference point A1 by the trapezius (compensation 1) extended and connected from the reference point A1 which is a should joint reference point and movement, to D2, of the median line D1, which is the central axis of the body, and thus, remeasurement may be performed.

As such, the first cause of the elevation compensation of the scapula when measuring the range of motion of the shoulder joint is presumed to be weakened shoulder abductor muscle or insufficient flexibility of the lats, and microdamage, asymmetry, imbalance, or adhesion the joint and resultant contraction of the trapezius muscle.

The second measurement method for measuring the shoulder joint motion range is described below.

In the shoulder abduction as shown in (b) of FIG. 9, the reference point A1 and the motion point A2 are shown as if they have been moved at 90 degrees with respect to the median line D1. However, for the actual angle at which the movement has occurred in the shoulder, the abduction joint motion range of the left shoulder, i.e., the actual motion range for the reference point A1 and the motion point A2-1 and the shoulder joint motion range according thereto may be precisely measured by excluding the angle between the median line D1 of the body and D2 formed as the median line is moved from the angle of the reference point A1 and the motion point A2-1.

The second cause of the compensation upon measuring the shoulder joint motion range is presumed to be movement of the center of body by the insufficient shoulder abduction.

The third measurement method for measuring the shoulder joint motion range is described below.

As shown in (a) of FIG. 9, the accurate joint motion range for the shoulder abduction requires the motion point A2-1 of the joint (elbow) adjacent to the reference point A1. However, the join request message seems to have increased due to the movement (flexion of elbow) of the connection point A2-2 which is the limb end joint point connected with the motion point A2-1 and, because this is precise measurement of the shoulder joint motion range, remeasurement may be performed.

The third cause of the compensation upon measuring the shoulder joint motion range is presumed to be body asymmetry caused by the movement of the connection point A2-2 which is the limb end for helping the reduced joint motion range.

The exercise feedback provider 130 may provide exercise recommendation information based on the measured body information, posture information, and joint motion range.

According to an embodiment, exercise feedback performs exercise on the low motion joint according to the motion range or the hyper motion range joint is provided according to the motion range of the normal joint. As such, exercise needs to be done according to the normal motion range criteria to reduce injury or pain. In the case of hypermobility, the loosened joint may be stabilized, and in the case of hypomobility, the stiff joint may turn mobile.

Upon doing complex joint exercise including motion of one or more joints, the joint motion range needs to have the mobility in the normal range. For example, during a squat exercise, three joints, including the hip joint, knee joint, and ankle joint, move. When performing a squat exercise, if one of the three joints has 70% mobility and the other two joints have 100% mobility, and the exercise is performed in a range of motion greater than 70%, then the joint with 70% mobility, as well as left-right symmetry, may be subjected to abnormal stress.

As a solution to this, according to an embodiment, the optimal exercise information for safely doing exercise may be fed back by identifying and evaluating the body information and the posture information before doing exercise, identifying asymmetry of the joint motion range by measuring a more precise joint motion range considering, e.g., compensation action upon measurement, and performing exercise on the low motion joint according to the motion range.

While the present disclosure has been shown and described with reference to exemplary embodiments of the system and method for measuring body information, posture information, and joint motion range, it will be apparent to those of ordinary skill in the art that various changes in form and detail may be made thereto without departing from the spirit and scope of the disclosure as defined by the following claims.

What is claimed is:

1. A system for measuring body information, posture information, and one of joints motion range, the system comprising:
   a target image display configured to form a skeleton image of a subject on a grid pattern with a predetermined unit length and coordinates via image processing by using a three-dimensional (3D) depth camera including at least one of stereo camera, time-of-flight (ToF) camera, and structured pattern camera, configured to specify, on the skeleton image, feature points corresponding to joints of the subject, a reference point corresponding to a measurement target among the feature points, and a motion point corresponding to one of joints moving with respect to the reference point, and wherein the target image display is configured to generate a connection line connecting the feature points, wherein the stereo camera generates a stereoscopic image using two two-dimensional (2D) image sensors and adopts a common 3D depth recognition sensor scheme, the ToF camera obtains the movement time information by measuring a delay or a phase shift of a modulated optical signal for all pixels constituting a scene, and the structured pattern camera is performed by an optical 3D scanning method that projects a structured set of light patterns to the target and capture the resultant image using an image sensor, and wherein the 3D camera adopts a sensing scheme of detecting the subject and mapping with distance and emits light pulses to the subject and measures the characteristics of the signal reflected by the subject by applying Kinect, light detection and ranging (LiDAR), laser detection and ranging (Ladar), time-of-flight (ToF), laser scanner, or laser radar to the 3D depth camera;
   an information processor configured to obtain the body information from the skeleton image using the feature points, the connection line, the grid pattern, and a gravity line and a median line of the subject, configured to evaluate the posture information according to a preset posture classification criterion, and configured to measure the joint motion range by tracking motion of the motion point with respect to the reference point, wherein the information processor is implemented as a circuit for performing its operations or functions; and
   an exercise feedback provider configured to provide exercise recommendation information based on the body information, the posture information, and the joint motion range in which the exercise recommendation information is provided,
   wherein the information processor includes:
   a body information obtaining unit obtaining the body information including left-right symmetry information and physical numerical information about the subject's body length, angle, or ratio from the skeleton image using the feature points, the connection line, the grid pattern, the gravity line, and the median line;
   a posture information evaluating unit obtaining and evaluating the posture information from the skeleton image according to the preset posture classification criterion, using the gravity line and the median line; and
   a joint motion range measuring unit configured to measure the joint motion range by tracking the motion of the motion point with respect to the reference point,
   wherein the joint motion range measuring unit is configured to remeasure the joint motion range by: (1) sensing motion of the feature points except for the reference point and except for the motion point of the feature points, or (2) excluding an angle for the motion from the measured joint motion range;
   wherein i) the joint motion range measuring unit is configured to remeasure the joint motion range upon sensing at least one of:
   a movement of the gravity line or the median line using the camera's image processing;
   and upon sensing a movement of a first connection point, except for the motion point, extended and connected via the connection line from the reference point among the feature points using the camera's image processing;
   ii) the joint motion range measuring unit is configured to measure the joint motion range by calculating a first angle formed by the motion of the motion point and a second angle formed by a movement of a second connection point and subtracting the second angle from the first angle upon sensing a movement of a second connection line adjacent to the reference point and connected via the connection line from the reference point among the feature points using the camera's image processing; or
   iii) the joint motion range measuring unit is configured to remeasure the joint motion range upon sensing a movement of a third connection point corresponding to a limb end joint adjacent to the motion point and connected via the connection line from the reference point among the feature points using the camera's image processing, and
   wherein the system provides the joint motion range by measuring a complementary movement in other body parts than the joint being measured, and the movement occurs on the sagittal plane, frontal plane, and horizontal plane, which is measured by the 3D depth camera.

2. A method for measuring body information, posture information, and one of joints motion range, the method comprising:
   a target image displaying step for forming a skeleton image of a subject on a grid pattern with a predetermined unit length and coordinates via image processing by using a 3D depth camera including at least one of stereo camera, time-of-flight (ToF) camera, and structured pattern camera, wherein the stereo camera generates a stereoscopic image using two two-dimensional (2D) image sensors and adopts a common 3D depth recognition sensor scheme, the ToF camera obtains the movement time information by measuring a delay or a phase shift of a modulated optical signal for all pixels constituting a scene, and the structured pattern camera is performed by an optical 3D scanning method that projects a structured set of light patterns to the target and capture the resultant image using an image sensor, and wherein the 3D camera adopts a sensing scheme of detecting the subject and mapping with distance and emits light pulses to the subject and measures the characteristics of the signal reflected by the subject by applying Kinect, light detection and ranging (LiDAR), laser detection and ranging (Ladar), time-of-flight (ToF), laser scanner, or laser radar to the 3D depth camera;

a target joint specifying step for specifying, on the skeleton image, feature points corresponding to joints of the subject, a reference point corresponding to a measurement target among the feature points, and a motion point corresponding to one of joints moving with respect to the reference point, and generating a connection line connecting the feature points;

a body information obtaining step for obtaining the body information from the skeleton image using the feature points, the connection line, the grid pattern, and a gravity line and a median line of the subject, wherein the body information obtaining step is performed by an information processor which is implemented as a circuit for performing its operations or functions and includes obtaining the body information including left-right symmetry information and physical numerical information about a body length of the subject, a body angle of the subject, or a body ratio of the subject from the skeleton image using the feature points, the connection line, the grid pattern, the gravity line, and the median line, and wherein the posture information evaluating step includes obtaining and evaluating the posture information from the skeleton image according to the preset posture classification criterion, using the gravity line and the median line;

a posture information evaluating step for evaluating the posture information according to a preset posture classification criterion preset using the feature points, the connection line, the grid pattern, the gravity line, and the median line;

a joint motion range measuring step for measuring the joint motion range by tracking motion of the motion point with respect to the reference point; and an exercise feedback providing step for providing exercise recommendation information based on the body information, the posture information, and the joint motion range, wherein the joint motion range measuring step includes measuring the joint motion range by tracking the motion of the motion point with respect to the reference point, wherein the joint motion range measuring step includes remeasuring a joint motion range by: (1) sensing motion of the feature points except for the reference point and except for the motion point of the feature points, or (2) excluding an angle for the motion from the measured joint motion range;

wherein the joint motion range measuring step includes:

i) remeasuring the joint motion range upon sensing at least one of:

a movement of the gravity line or the median line using the camera's image processing;

and upon sensing a movement of a first connection point, except for the motion point, extended and connected via the connection line from the reference point among the feature points using the camera's image processing;

ii) measuring the joint motion range by calculating a first angle formed by the motion of the motion point and a second angle formed by a movement of a second connection point and subtracting the second angle from the first angle upon sensing a movement of a second connection line adjacent to the reference point and connected via the connection line from the reference point among the feature points using the camera's image processing; or iii) remeasuring the joint motion range upon sensing a movement of a third connection point corresponding to a limb end joint adjacent to the motion point and connected via the connection line from the reference point among the feature points using the camera's image processing; and wherein the system provides the joint motion range by measuring a complementary movement in other body parts than the joint being measured, and the movement occurs on the sagittal plane, frontal plane, and horizontal plane, which is measured by the 3D depth camera.

* * * * *